US00PP31223P2

(12) United States Plant Patent
Hansen

(10) Patent No.: US PP31,223 P2
(45) Date of Patent: Dec. 10, 2019

(54) ***HEUCHERA* PLANT NAMED 'LEMON LOVE'**

(50) Latin Name: ***Heuchera* hybrid**
Varietal Denomination: Lemon Love

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 15/998,375

(22) Filed: Aug. 10, 2018

(51) Int. Cl.
*A01H 5/02* (2018.01)
*A01H 6/80* (2018.01)

(52) U.S. Cl.
USPC ..... Plt./440

(58) Field of Classification Search
USPC ..... Plt./440

CPC ... A01H 5/02; A01H 5/12; A01H 5/22; A01H 5/025; A01H 6/80; A01H 5/00
See application file for complete search history.

(56) References Cited

PUBLICATIONS

Terra Nova Nurseries Patent List 2019, retrieved on Jun. 3, 2019, retrieved from the Internet at http://www.terranovanurseries.com/resources/patent-list/, pp. 1, 10, 18. (Year: 2019).*

* cited by examiner

*Primary Examiner* — June Hwu

(57) ABSTRACT

The new and distinct hybrid of *Heuchera* plant named 'Lemon Love' with rounded leaf blades, moderately dissected, slightly sinuate, of bright yellow in spring becoming chartreuse in summer. The new plant has pink-tipped calyces on mostly upright highly branched panicles. The new plant is vigorous, and produces large clumps with many dense leaves and is useful in the landscape or in containers.

1 Drawing Sheet

Botanical denomination: *Heuchera* hybrid.
Variety denomination: 'Lemon Love'.

BACKGROUND OF THE INVENTION

The present invention relates to a new and distinct cultivar of Coral Bells in the Saxifragaceae family and given the cultivar name of 'Lemon Love'. *Heuchera* 'Lemon Love' was hybridized by the inventor on Apr. 24, 2013 at a wholesale perennial nursery in Zeeland, Mich., USA and assigned the breeder code 13-798-6. The seed or female parent was *Heuchera* 'Citronelle' U.S. Plant Pat. No. 17,934 and the pollen or male parent was *Heuchera* 'Coral Forest' (not patented).

*Heuchera* 'Lemon Love' was first selected in the fall of 2015 and passed final evaluation in the fall of 2016 from among thousands of other seedlings from the same cross and hundreds of other crosses. *Heuchera* 'Lemon Love' has been asexually propagated by division at the same nursery in Zeeland, Mich. in 2015 and by careful shoot tip tissue culture propagation, and the resultant plants have remained stable and continued to exhibit the same characteristics as the original plant for multiple generations.

No plants of *Heuchera* 'Lemon Love' have been sold, in this country or anywhere in the world, prior to the filing of this application, nor has any disclosure of the new plant been made prior to the filing of this application with the exception of that which was disclosed within one year of the filing of this application, and was either derived directly or indirectly from the inventor.

BRIEF SUMMARY OF THE INVENTION

The following traits distinguish *Heuchera* 'Lemon Love' as a distinct hybrid plant. In comparison to the female parent, *Heuchera* 'Lemon Love' has more ruffled, brighter lemon yellow-colored foliage compared to the flatter and more chartreuse foliage of 'Citronelle'. 'Coral Forest' has flatter, green foliage with maroon-colored area surrounding the veins and red flowers in comparison with that of the new plant. Other similar cultivars include: 'Lemon Chiffon' U.S. Plant Pat. No. 19,033 and 'Tnheuls' U.S. Plant Pat. No. 30,843 and 'Pear Crisp' U.S. Plant Pat. No. 23,568. 'Lemon Chiffon' has foliage that is less sinuate, slightly less dissected. 'Tnheuls' has less dense foliage and the flowers are white. 'Pear Crisp' has foliage that is more deeply dissected, more ovate and the flowers are white and not light pink. 'Pretty Pistachio' U.S. Plant Pat. No. 29,361 has flowers that are larger and more pinkish, and the flowers are denser on the panicles.

*Heuchera* 'Lemon Love' differs from its parents as well as all other coral bells known to the applicant in the following combined traits:

1. The large rounded leaf blades are moderately dissected and slightly sinuate near margins.
2. Leaves are bright yellow in spring and become chartreuse in summer with upper and lower surfaces matte.
3. Produces flowers with pink-tipped calyxes beginning early summer on heavily branched panicles.
4. Stems are densely covered with leaves.
5. Produces large clumps and many large individual leaves.
6. Plant is vigorous.

BRIEF DESCRIPTION OF THE DRAWINGS

The photographs of the new plant demonstrate the overall appearance of the plant including the unique traits. The colors are as accurate as reasonably possible with modern color reproductions. Some slight variation of color may occur as a result of lighting quality, intensity, wavelength, and direction or reflection.

DETAILED BOTANICAL DESCRIPTION

Figure 1:
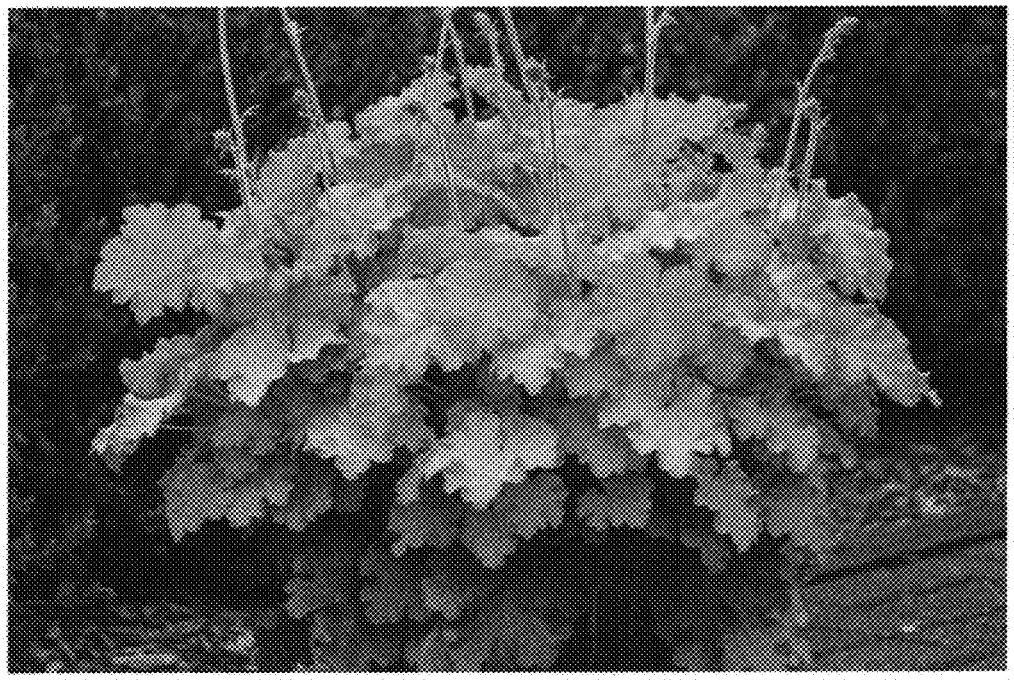
FIG. 1 shows a two-year-old plant just before flowering with light yellow spring foliage color.
Figure 2:
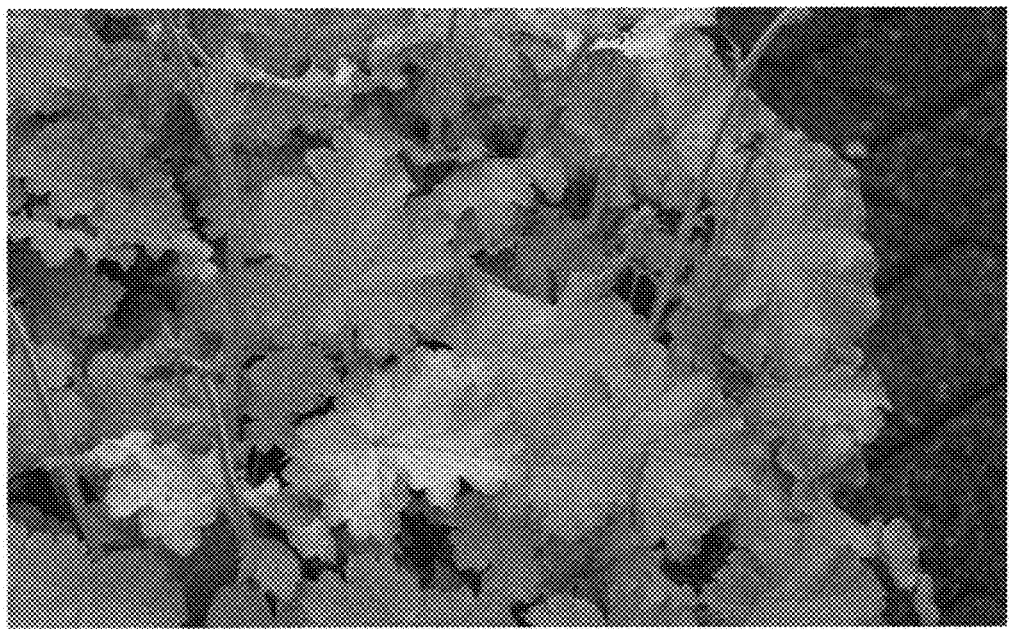
FIG. 2 shows a close-up of the foliage and flower scapes.

The following description is based on a two-year-old plant growing in a lightly shaded greenhouse in Zeeland, Mich., USA. The new plant has not been grown under all possible environments and may phenotypically appear different under different conditions such as light, temperatures, fertilizer, and water, without any difference in genotype. The color descriptions used are from the 2015 edition of The Royal Horticultural Society Colour Chart except where common dictionary terms are used.

Parentage: Female or seed parent was *Heuchera* 'Citronelle' and the male or pollen parent was 'Coral Forest';

Plant habit: Hardy herbaceous perennial with basal rosette of foliage; mounded foliage about 25 cm tall and 60 cm in diameter with scapes to about 55 cm tall; stems to about 4.5 cm long and 18.0 mm diameter at base completely covered with petiole stipules, with about 18 leaves per stem and 12 main stems per plant;

Roots: Fibrous, finely branched;

Growth rate: Vigorous, rapid; rooting from cutting in two weeks and finishing in three-liter container in about 3 months;

Foliage: Rounded; shallowly penta-lobed; mostly flat, slightly sinuate along margins in spring, marginal undulation weak in summer; apex and lobe apices apiculate; base cordate, margin crenate and ciliolate; adaxial surface micro-puberulent, abaxial pubescent; shallowly lobed; many indentations; glossiness very weak adaxial and abaxial;

Leaf blade size: To about 12.0 cm wide and 12.5 cm long, average about 10.5 cm wide and 10.5 cm long;

Leaf color: Spring and young emerging leaves adaxial nearest RHS 145A and with no silver or dark green marbling surrounding the veins, spring young emerging leaves abaxial nearest RHS 144A to RHS 160A toward petiole and RHS 144A toward margin; mature mid-season leaves adaxial blend nearest RHS 145C and RHS 147D; midseason abaxial nearest RHS 147D; leaves are not typically persistent through winters in Michigan so no late season coloration has been observed;

Leaf quantity: Dense, about 230 per plant;

Veins: Palmate, hirsutulous abaxial and puberulent adaxial; costate abaxial and nearly flat adaxial;

Vein color: On emerging or early spring foliage adaxial blend nearest RHS 145A with emerging or early spring abaxial nearest RHS 145C; mid-season and flowering time adaxial variable, nearest RHS 160A toward petiole and RHS 144A distally; mid-season and flowering time abaxial main veins nearest RHS 145C and secondary veins nearest RHS 145A;

Petiole: Terete, base amplexicaul; straight, stiff; outwardly to drooping with outer leaves and slightly upright with inner leaves; with pubescent hairs to about 3.0 mm long; average about 25.0 cm long and about 3.2 mm diameter above stipule and 7.0 mm across at base including stipule;

Petiole color: Emerging leaf nearest RHS N144D; mature leaf nearest RHS 145A;

Stipule: At base of petiole; puberulent abaxial and glabrous adaxial; about 20.0 mm long and about 8.0 cm wide at base with two distally-flared acute appendages about 2.0 mm long;

Stipule color: Adaxial nearest RHS 145C with two longitudinal stripes about 1.0 mm long running 1.0 mm inside of margin of nearest RHS 145B and margin nearest RHS 145C; abaxial nearest RHS 145C with two longitudinal stripes about 1.0 mm long running 1.0 mm inside of margin of nearest RHS 145B and margin nearest RHS 145C;

Peduncle: Panicle; terete; stiff; pubescent; mostly upright; to about 57.0 cm long and 3.0 mm diameter at base, average about 52 cm tall and about 3.0 mm diameter; about twenty per plant with up to 280 flowers per panicle, average about 240; heavily-branched panicle with up to 22 branches per peduncle up to about 6.5 cm long and about 1.0 mm diameter decreasing near distal end, average 20 branches per panicle; branches outwardly at about 45 degree angle to main peduncle; flower density moderate;

Flowering longevity: Panicle effective for about five weeks;

Flower density: Medium;

Peduncle color: Lighter than RHS 146D; sometimes blushed with RHS 182A to RHS 182B;

Pedicel: Terete, finely puberulent, average about 2.0 mm long and 0.5 mm diameter;

Pedicel color: Blend between RHS 157D and RHS 159D, with proximal tinting of nearest RHS 182B;

Buds one day prior to opening: Oblong ellipsoidal; rounded apex and rounded base; puberulent; about 5.0 mm long and 2.5 mm diameter;

Bud color one day prior to opening: Proximal portion nearest RHS 145D, becoming nearest RHS 186D toward center and blend of nearest RHS 186C and RHS 182D toward apex;

Flower: Perfect, campanulate, actinomorphic, about 7.0 mm long and 5.0 mm in diameter at face; individual flowers lasting about 4 days on plant or as cut flower; rarely persistent;

Flower attitude: Mostly outwardly to slightly drooping;

Calyx: Five sepals; apex acute; about 5.0 mm long and 5.0 mm wide, base fused in proximal 4.5 mm to form hypanthium; pubescent abaxial, glabrous adaxial; rarely persistent;

Calyx color: Abaxial base blend between RHS 146D and RHS 160D and distally nearest RHS N155C and RHS 182A at apex; adaxial apex between RHS 182A and RHS 182B; proximally lightening to nearest RHS N155C at base;

Petals: Five, oblanceolate to spatulate, acute apex and attenuate base; margin entire, glabrous abaxial and adaxial; about 3.5 mm long and 1.0 mm wide at middle;

Petal color: Abaxial and adaxial nearest RHS NN155D;

Androecium: Five adnate to adaxial calyx about 1.0 mm above base;

*Filaments*.—Five, thin, glabrous; about 1.5 mm long and less than 0.3 mm diameter; color translucent to nearest RHS NN155C.

*Anthers*.—Ellipsoidal, distinct, basifixed, longitudinal; color nearest RHS 161B.

*Pollen*.—Abundant; color nearest RHS 8D.

Gynoecium: One, two-beaked; half-inferior; bifid style with pistil split at ovary; 6.0 mm long;

*Style*.—Bifid; exserted; split apart at apex of ovary; about 4.5 mm long and about 0.5 mm diameter; color nearest RHS NN155B.

*Stigma*.—Acute apex, about 0.1 mm diameter; color nearest RHS NN155B.

*Ovary*.—Half-inferior, about 2.5 mm long and 2.0 mm diameter; ellipsoidal to globose; apex acute, base rounded; color between RHS 150D and RHS 145D.

Fruit: Two-beaked ellipsoidal capsule; about 3.0 mm long and 1.7 mm across; color nearest RHS 200B;

Seed: Thin ellipsoidal; less than 1.0 mm long and less than 0.5 mm wide; color between RHS 202A and RHS 200A;

Disease and pest tolerance: The new plant grows best with ample moisture and drainage in either sun or shade. Cold hardy from USDA zones 4 to 9. Other resistance and tolerance outside of that normal for *Heuchera* is not known.

It is claimed:

1. The new and distinct coral bells plant named *Heuchera* 'Lemon Love' as herein described and illustrated.

* * * * *